US 12,004,808 B2

(12) United States Patent
Hofvander (10) Patent No.: US 12,004,808 B2
(45) Date of Patent: *Jun. 11, 2024

(54) DETERMINATION PROCESS AND PREDICTIVE CLOSED-LOOP CONTROL OF DOSIMETRY USING MEASUREMENT OF SKIN SURFACE TEMPERATURE AND ASSOCIATED METHODS

(71) Applicant: Accure Acne Inc., Boulder, CO (US)

(72) Inventor: Henrik Hofvander, Budapest (HU)

(73) Assignee: Accure Acne, Inc., Boulder, CO (US)

( * ) Notice: Subject to any disclaimer, the term of this patent is extended or adjusted under 35 U.S.C. 154(b) by 79 days.

This patent is subject to a terminal disclaimer.

(21) Appl. No.: 17/735,056

(22) Filed: May 2, 2022

(65) Prior Publication Data

US 2022/0354576 A1 Nov. 10, 2022

Related U.S. Application Data

(63) Continuation of application No. 16/658,818, filed on Oct. 21, 2019, now Pat. No. 11,317,969.

(Continued)

(51) Int. Cl.
*A61B 18/20* (2006.01)
*A61B 17/00* (2006.01)
*A61B 18/00* (2006.01)

(52) U.S. Cl.
CPC .. *A61B 18/203* (2013.01); *A61B 2017/00199* (2013.01); *A61B 2017/00973* (2013.01);
(Continued)

(58) Field of Classification Search
CPC ........ A61B 18/203; A61B 2017/00199; A61B 2017/00973; A61B 2018/00029;
(Continued)

(56) References Cited

U.S. PATENT DOCUMENTS 5,968,034 A 10/1999 Fullmer et al.
6,050,990 A 4/2000 Tankovich et al.
(Continued)

FOREIGN PATENT DOCUMENTS

GB 2410690 A 8/2005
WO 2005074830 A2 8/2005
(Continued)

OTHER PUBLICATIONS

Sakamoto, et al., "Selective Photothermolysis to Target Sebaceous Glands: Theoretical Estimation of Parameters and Preliminary Results Using a Free Electron Laser", Lasers in Surgery and Medicine 44:175-183 (2012).
(Continued)

*Primary Examiner* — Aaron F Roane
(74) *Attorney, Agent, or Firm* — Neugeboren O'Dowd PC (57) ABSTRACT

A method for determining parameters for operating a light source within a photo-thermal targeted treatment system is disclosed. The method includes cooling a treatment location, administering first laser pulses at the treatment location, the first laser pulses having thermal energy below a known damage threshold, tracking skin surface temperatures at the treatment location while administering the first laser pulses, estimating a relationship between parameters for operating the light source and the skin surface temperature by fitting tracked skin surface temperature to a correlation model, determining a safe operating range for the light source to avoid thermal damage at the treatment location while still effectively targeting the chromophore, administering second laser pulses at the treatment location, the second laser pulses staying within the safe operating range for the light source, and adjusting the light source according to the tracked skin surface temperatures to stay within the safe operating range.

18 Claims, 8 Drawing Sheets

Related U.S. Application Data (60) Provisional application No. 62/771,523, filed on Nov. 26, 2018, provisional application No. 62/749,104, filed on Oct. 22, 2018.

(52) U.S. Cl.
CPC ........... *A61B 2018/00029* (2013.01); *A61B 2018/0047* (2013.01); *A61B 2018/00577* (2013.01); *A61B 2018/00702* (2013.01); *A61B 2018/00791* (2013.01); *A61B 2018/00803* (2013.01); *A61B 2018/00988* (2013.01)

(58) Field of Classification Search
CPC .. A61B 2018/0047; A61B 2018/00577; A61B 2018/00702; A61B 2018/00791; A61B 2018/00803; A61B 2018/00988
USPC ............................................................ 606/9
See application file for complete search history.

(56) References Cited

U.S. PATENT DOCUMENTS

| | | |
|---|---|---|
| 6,190,377 B1 | 2/2001 | Kuzdrall |
| 6,413,255 B1 | 7/2002 | Stern |
| 6,436,094 B1 | 8/2002 | Reuter |
| 6,451,007 B1 | 9/2002 | Koop et al. |
| 7,056,318 B2 | 6/2006 | Black |
| 7,413,572 B2 | 8/2008 | Eimerl et al. |
| 8,291,913 B2 | 10/2012 | Eimerl et al. |
| 11,318,324 B2 | 5/2022 | Kim et al. |
| 11,389,238 B2 | 7/2022 | Franceschina et al. |
| 2002/0091377 A1 | 7/2002 | Anderson et al. |
| 2003/0055414 A1 | 3/2003 | Altshuler et al. |
| 2005/0107850 A1 | 5/2005 | Vaynberg et al. |
| 2007/0191827 A1 | 8/2007 | Lischinsky et al. |
| 2010/0174223 A1 | 7/2010 | Sakamoto et al. |
| 2013/0178916 A1 | 7/2013 | Rylander et al. |
| 2014/0121631 A1 | 5/2014 | Bean et al. |
| 2014/0243804 A1 | 8/2014 | Lukac et al. |
| 2014/0371736 A1 | 12/2014 | Levin et al. |
| 2019/0262072 A1 | 8/2019 | Sakamoto et al. |
| 2019/0374791 A1 | 12/2019 | Tagliaferri et al. |
| 2020/0391051 A1 | 12/2020 | Daly et al. |
| 2022/0354576 A1 | 11/2022 | Hofvander |
| 2023/0000553 A1* | 1/2023 | Hofvander ........... A61B 18/203 |

FOREIGN PATENT DOCUMENTS

| | | |
|---|---|---|
| WO | 2015117005 A1 | 8/2015 |
| WO | 2017005628 A1 | 1/2017 |
| WO | 2018076011 A1 | 4/2018 |

OTHER PUBLICATIONS

Extended European Search Report, European Patent Application 19877178.4-1126, dated Jun. 22, 2022.

Korean Patent Office, "Notice of Allowance for Korea Patent Application No. 10-2021-7015202," Jan. 13, 2023, 3 pages.

Roane, Aaron F, "Non-Final Office Action for U.S. Appl. No. 17/735,046", dated Oct. 5, 2023, 9 pages.

China Patent Office, "Office Action Regarding Chinese Patent Application No. 201980076865.7", Dec. 21, 2023, Published in: CN [Translation attached].

* cited by examiner

FIG. 8

DETERMINATION PROCESS AND PREDICTIVE CLOSED-LOOP CONTROL OF DOSIMETRY USING MEASUREMENT OF SKIN SURFACE TEMPERATURE AND ASSOCIATED METHODS

PRIORITY CLAIM

The present application is a continuation of copending U.S. patent application Ser. No. 16/658,818, filed Oct. 21, 2019 and entitled "Dosimetry Determination Process via Measurement of Skin Surface Temperature and Associated Methods," which claims the benefit of U.S. Provisional Patent Application Ser. No. 62/749,104, filed Oct. 22, 2018 and entitled "Dosimetry Determination Process via Measurement of Skin Surface Temperature and Associated Methods," as well as U.S. Provisional patent Application Ser. No. 62/771,523, filed Nov. 26, 2018, entitled "Predictive Closed-Loop Control of Dosimetry Using Measurement of Skin Surface Temperature and Associated Methods," which applications are incorporated herein by reference in their entirety.

FIELD OF THE INVENTION

The present invention relates to photo-thermal targeted treatment and, more specifically, systems and methods for determining the correct dosimetry for photo-induced thermal treatment targeting specific chromophores embedded in a medium.

BACKGROUND OF THE INVENTION

Chromophores embedded in a medium such as the dermis, can be thermally damaged by heating the chromophore with a targeted light source, such as a laser. However, the application of enough thermal energy to damage the chromophore can also be damaging to the surrounding dermis and the overlying epidermis, thus leading to epidermis and dermis damage as well as pain to the subject. This problem also applies to targets, such as sebaceous glands, where a chromophore such as sebum is used to heat the target to a high enough temperature to cause damage to the target.

Previous approaches to prevent epidermis and dermis damage, as well as subject pain include:
1. Pre-cooling the epidermis, then applying the photo-thermal treatment; and
2. Pre-cool the epidermis, also pre-condition (i.e., pre-heat) the epidermis and dermis in a preheating protocol, then apply photo-thermal treatment in a distinct treatment protocol. In certain instances, the preheating protocol and the treatment protocol are performed by the same laser, although the two protocols involve different laser settings and application protocols, thus leading to further complexity in the treatment protocol and equipment.

SUMMARY OF THE INVENTION

In accordance with the embodiments described herein, there is disclosed a method for determining a suitable set of parameters for operating a light source within a photo-thermal targeted treatment system for targeting a chromophore embedded in a medium. The method includes, prior to administering a treatment protocol to a first subject, 1) administering at least one laser pulse at a preset power level to a first treatment location, where the preset power level is below a known damage threshold. The method also includes 2) measuring a skin surface temperature at the first treatment location, following administration of the at least one laser pulse. The method further includes 3) estimating a relationship between the parameters for operating the light source and the skin surface temperature at the first treatment location, and 4) defining a safe operating range for the parameters for operating the light source in order to avoid thermal damage to the medium at the first treatment location while still effectively targeting the chromophore in administering the treatment protocol.

In an embodiment, steps 1) through 4) are repeated at a second treatment location on the first subject prior to administering the treatment protocol at the second treatment location. In another embodiment, steps 1) through 4) are repeated at the first treatment location on a second subject prior to administering the treatment protocol on the second subject. In still another embodiment, the method further includes 5) storing in a memory of the photo-thermal targeted treatment system the safe operating range for the parameters for operating the light source for the first subject at the first treatment location, and 6) when administering the treatment protocol on the first subject at a later time, taking into consideration the parameters so stored in the memory.

In another embodiment, a photo-thermal targeted treatment system for targeting a chromophore embedded in a medium is disclosed. The system includes a light source configured for providing laser pulses over a range of power levels when operated using a set of parameters, the range of power levels including a known damage threshold for the chromophore and a treatment location. The system also includes a temperature measurement apparatus for measuring a skin surface temperature at the treatment location, and a controller for controlling the light source and the temperature measurement apparatus. The controller is configured for estimating a relationship between the parameters of the light source and the skin surface temperature at the treatment location, defining a safe operating range for the set of parameters of the light source in order to avoid thermal damage to the medium at the treatment location while still effectively targeting the chromophore in administering the treatment protocol, and setting the light source to administer the laser pulses within the safe operating range.

In yet another embodiment, a method for adjusting a suitable set of parameters for operating a light source within a photo-thermal targeted treatment system for targeting a chromophore embedded in a medium during administration of a treatment protocol to a first subject at a first treatment location is disclosed. The method includes: 1) measuring the skin surface temperature at the first treatment location at least once; 2) predicting skin temperature as the treatment protocol is administered to the first subject at the first treatment location; and 3) adjusting at least one of the parameters for operating the light source such that a future measurement of the skin surface temperature at the first treatment location will not exceed a specified value. Predicting skin temperature considers at least one of a heat transfer model and a series of experimental results.

DETAILED DESCRIPTION OF EMBODIMENTS OF THE INVENTION

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Figure 1:
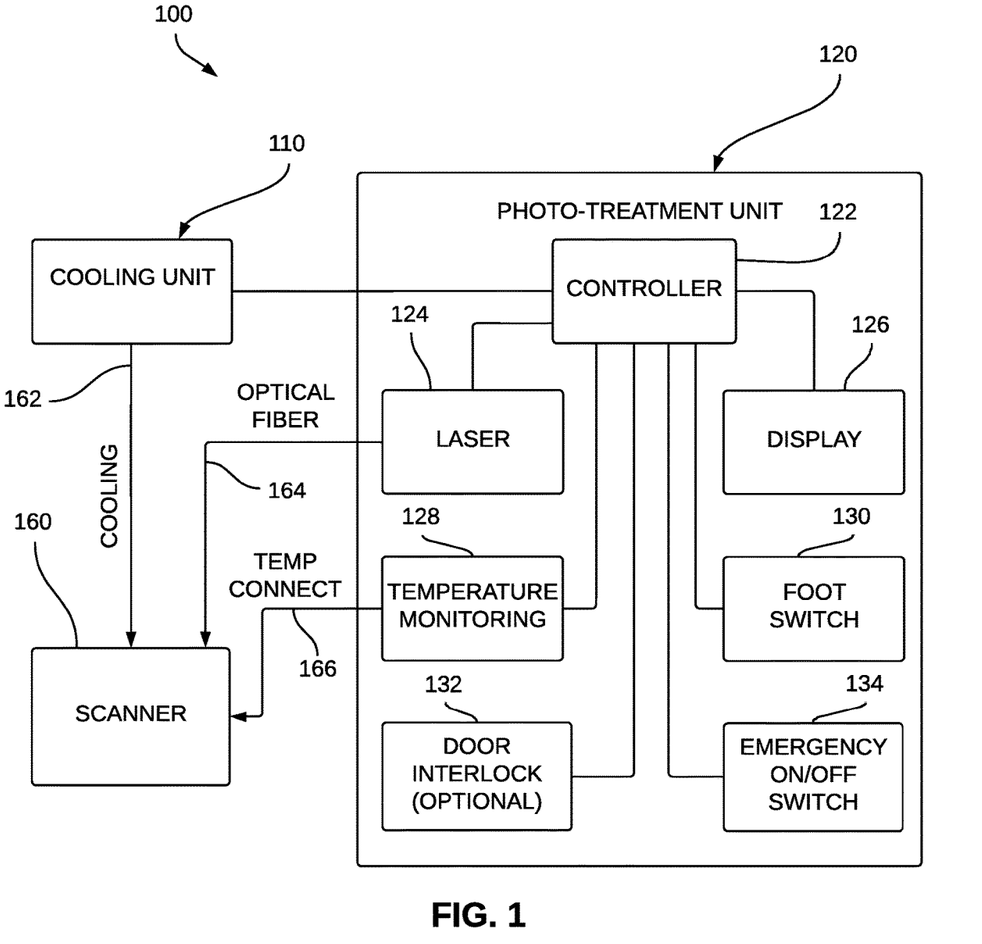
FIG. 1 illustrates an exemplary photothermal targeting treatment system, in accordance with an embodiment.

FIG. 1 shows an exemplary photo-thermal targeted treatment system for targeting a target, wherein the target includes specific chromophores embedded in a medium, and heating the target to a sufficiently high temperature so as to damage the target without damaging the surrounding medium. The system can be used, for example, for photo-thermal ablation of sebaceous glands in a targeted fashion, where sebum is the chromophore embedded within the sebaceous gland, while sparing the epidermis and dermis surrounding the target sebaceous glands.

Still referring to FIG. 1, a photo-thermal targeted treatment system 100 includes a cooling unit 110 and a photo-treatment unit 120. Cooling unit 110 provides a cooling mechanism for a cooling effect, such as by contact or by direct air cooling, to treatment area, namely the outer skin layer area overlying the target sebaceous gland. Cooling unit 110 is connected with a controller 122 within photo-treatment unit 120. It is noted that, while controller 122 is shown to be contained within photo-treatment unit 120 in FIG. 1, it is possible for the controller to be located outside of both cooling unit 110 and photo treatment unit 122, or even within cooling unit 110.

Controller 122 further controls other components within photo-treatment unit 120, such as a laser 124, a display 126, a temperature monitoring unit, a foot switch 130, a door interlock 132, and an emergency on/off switch. Laser 124 provides the laser power for the photo-treatment protocol, and controller 122 regulates the specific settings for the laser, such as the output power and pulse time settings. Laser 124 can be a single laser or a combination of two or more lasers. If there more than one laser is used, the laser outputs are combined optically to function as one more powerful laser. Display 126 can include information such as the operating conditions of cooling unit 110, laser 124, and other system status. Temperature monitoring unit 128 is used to monitor the temperature of the skin surface in the treatment area, for example, and the measured skin surface temperature at the treatment area is used by controller 122 to adjust the photo-treatment protocol. Controller 122 also interfaces with footswitch 130 for remotely turning on or off laser 124 and/or cooling unit 110. Additionally, door interlock 132 can be used as an additional safety measure such that, when the door to the treatment room is ajar, door interlock 132 detects the condition and instructs controller 122 to not allow photo-treatment unit 120, or at least laser 124, to operate. Furthermore, emergency on/off switch 134 can be provided to quickly shut down photo-thermal targeted treatment system 100 in case of an emergency. In another modification, additional photodiodes or other sensors can be added to monitor the power level of the energy emitted from laser 124.

Continuing to refer to FIG. 1, photo-thermal targeted treatment system 100 further includes a scanner 160, which is the portion of the device handheld by the user in applying the treatment protocol to the subject. Scanner can be formed, for example, in a gun-like or stick-like shape for ease of handling by the user. Scanner 160 is connected with cooling unit 110 via a cooling connection 162, such that the cooling protocol can be applied using scanner 160. Additionally, the output from laser 124 is connected with scanner 160 via an optical fiber delivery 164, such that the photo-treatment protocol can be applied using scanner 160. Scanner 160 is connected via a temperature connection 166 to temperature monitoring unit 128, so as to feedback the skin temperature at the treatment area, for example, to controller 122.

Figure 2:
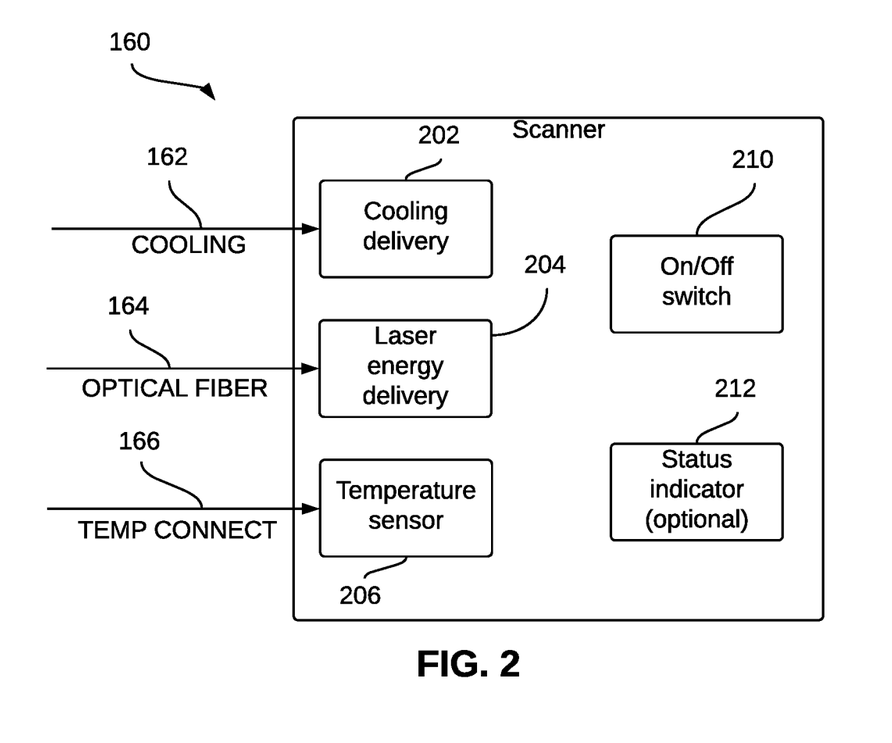
FIG. 2 illustrates an exemplary scanner arrangement for use with the photothermal targeting treatment system, in accordance with an embodiment.

FIG. 2 shows further details of scanner 160, in accordance with an embodiment. Cooling connection 162 is connected with a cooling delivery unit 202, which is configured to deliver the cooling mechanism (e.g., a cold air stream) to the treatment area. Optical fiber delivery 164, from laser 124, is connected with a laser energy delivery unit 204, which includes optical components for delivering light energy for the photo-thermal treatment protocol to the treatment area. Finally, temperature connection 166 is connected with a temperature sensor 206, which measures the temperature at the treatment area for feedback to controller 122. Additionally, scanner 160 includes an on/off switch 210 (such as a trigger switch to turn on/off laser 124) and, optionally, a status indicator 212, which indicates the operational status of scanner 160, such as if the laser is being operated. While scanner 160 is schematically shown as a box in FIG. 2, the actual shape is configured for ease of use. For example, scanner 160 can be shaped as a nozzle with a handle, a handgun shape, or another suitable shape for ease of aiming and control by the user.

In an exemplary usage scenario, the full treatment area overlying the sebaceous glands to be treated is cooled. The cooling protocol can include, for example, the application of a cold airstream across the treatment area for a prescribed time period, such as 10 seconds. Following pre-cooling, the cooling mechanism (e.g., cold airstream or contact-cooling) remains active and a photo-treatment protocol is applied to the treatment area. In one embodiment, pulses of a square, "flat-top" beam is used in combination with a scanner apparatus to sequentially apply a laser pulse to the treatment area. For example, the photo-treatment protocol can include the application of a set number of light pulses onto each segment of the treatment area, with the segments being sequentially illuminated by the laser pulses. In another embodiment, the segments are illuminated in a random order.

Figure 3:
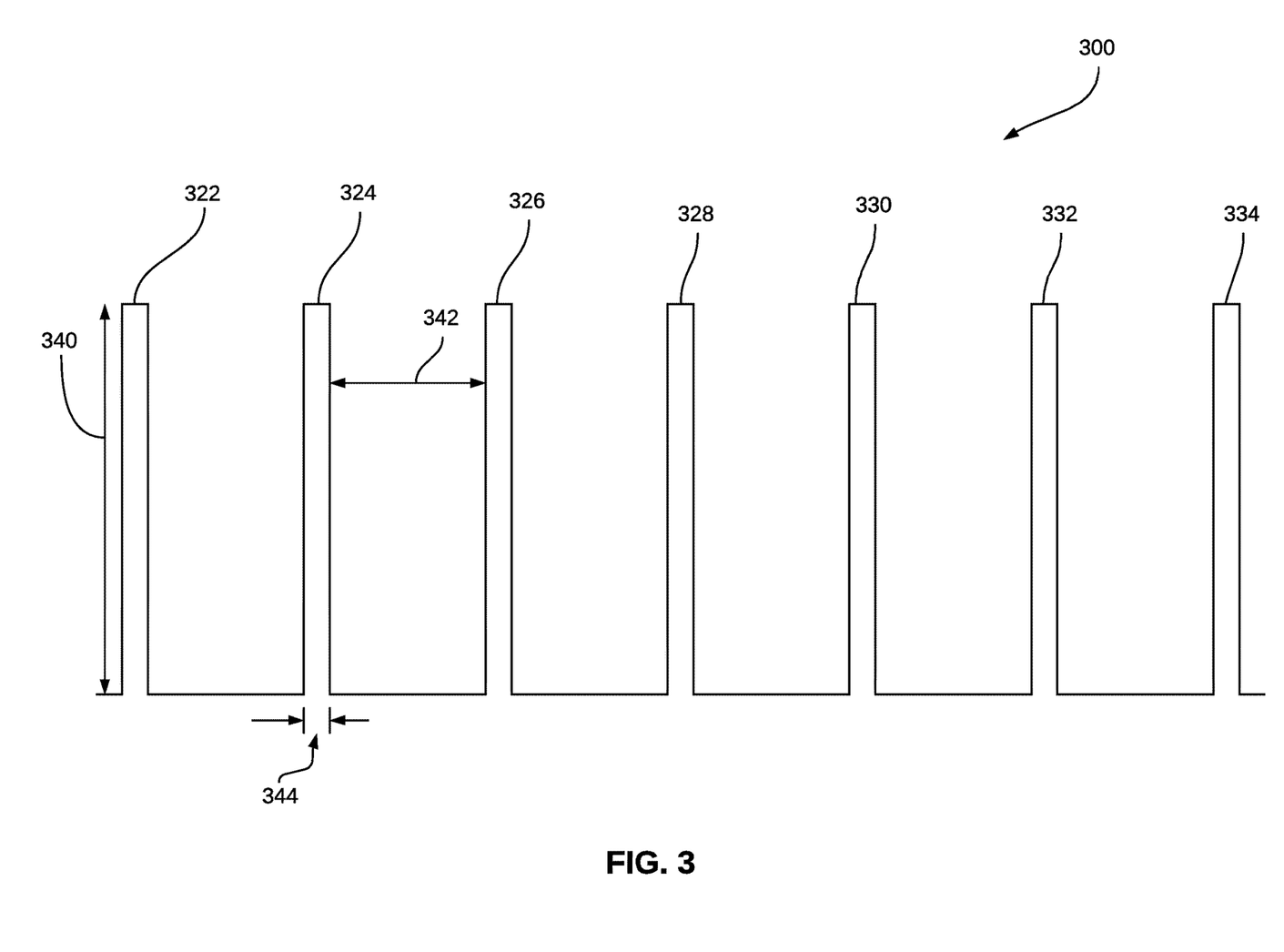
FIG. 3 shows a schematic of an exemplary set of light pulses suitable for use as the integrated pre-conditioning/photo-treatment protocol, in accordance with an embodiment.

An example of a set of pulses suitable for a conditioning/photo-treatment protocol is illustrated in FIG. 3, in accordance with an embodiment. A sequence 300 includes light pulses 322, 324, 326, 328, 330, 332, and 334 that are applied at the treatment area. In one embodiment, all of the seven light pulses are of equal power, and are separated by a uniform pulse separation (represented by a double-headed arrow 342), and have the same pulse duration (represented by a gap 344). In an example, pulse duration 344 is 150 milliseconds, and the pulse separation is 2 seconds. The 2 second pulse separation is intended, for example, to allow the epidermis and dermis in the block to cool down so as to prevent damage thereto. During the pulse separation time period, the laser can be scanned over to a different segment within the treatment area so as to increase the laser use efficiency. It is noted that FIG. 3 is not drawn to scale.

Figure 4:
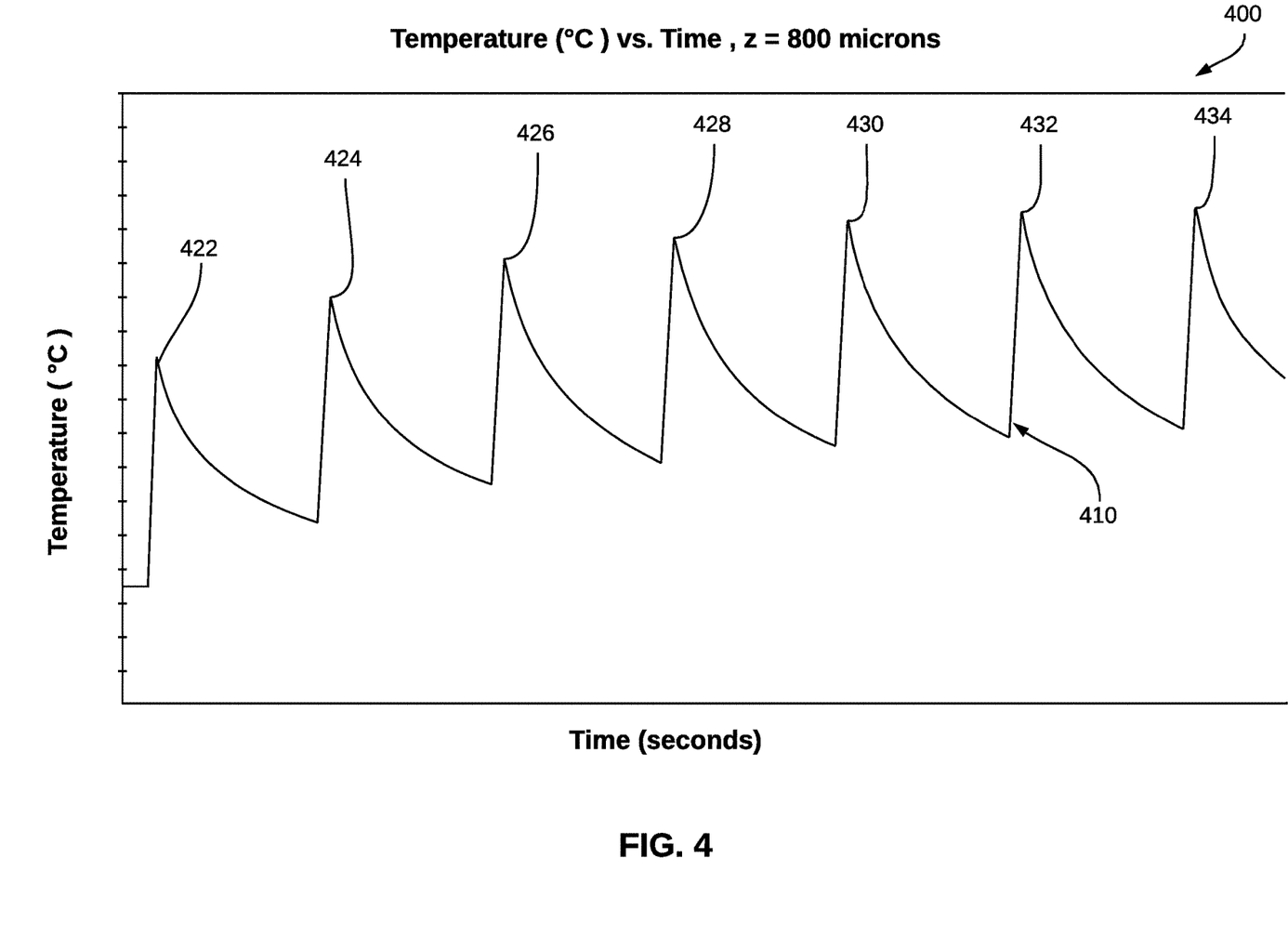
FIG. 4 shows the measured temperature at the skin surface as a function of time as the treatment photo pulses are applied thereto, in accordance with an embodiment.

FIG. 4 shows the measured skin surface temperature as light pulses, such as those shown in FIG. 3, are applied to the treatment area, in accordance with an embodiment. In the example shown in FIG. 4, the treatment area had been pre-cooled by direct air cooling for 7 seconds, then light pulses from a 1720 nm wavelength laser at 22 watts power and 150 milliseconds in duration were applied with a period of 2 seconds, while the cooling remains on. In this particular example, the direct-air cooling used for the cooling and during the treatment, delivers a high speed column of air, cooled to −22° C., resulting in a heat transfer coefficient between the skin and the air of approximately 350 W/m^2 K. The beam size is 4.9 mm square, in an embodiment. The exact beam size can be adjusted, using for example collimation optics, depending on the size of the treatment area, power profile of the laser, the location of the treatment area of the body, and other factors.

The resulting changes in skin surface temperature are shown in a graph 400, where a peak 422 corresponds to the application light pulse 322 as shown in FIG. 3, and similarly for peaks 424, 426, 428, and 430. In example shown in FIG. 4, the average power per spot is 22 W*0.15 s/2 s=1.65 W. The same average power per spot can be achieved, for instance, by pulsing at 33 watts for 100 ms with a pulse separation of 2 s, or by pulsing at 25.1 W for 125 ms with a pulse separation of 1.9 s. Furthermore, the average laser power per area should be in balance with the heat extraction achieved by the cooling system.

The requirements for successful photo-thermal targeted treatment of specific chromophores with minimum subject discomfort include: 1) Epidermis sparing, namely making sure that the peak temperature value at the skin surface is less than around 55° C.; 2) Dermis sparing, namely avoiding overheating the dermis by balancing the peak and average power of the treatment pulses with the heat extraction of the cooling system; and 3) Selective heating of the chromophore, and the target containing the chromophore, such as a peak temperature greater than 55° C. for sebaceous gland treatments. It is noted that the peak temperature value of 55° C. is highly dependent on the specific treatment protocol, and is adjustable to other temperatures to stay within a safe operating range to avoid damaging the surrounding dermis and epidermis.

It is known in the literature that tissue parameters, such as the thickness of the epidermis and dermis, vary among individuals, according to factors such as age, gender, and ethnicity, as well as between different skin locations on the body. For example, the forehead has different tissue properties than the back, even for the same individual, thus necessitating different treatment parameter settings for the different treatment locations. Consideration of such variations in tissue properties in determining the specific treatment protocol is significant for laser-based treatment of acne. Additionally, there may be variations in, for instance, the exact laser power, spot size, and cooling capacity between specific laser systems due to manufacturing variability and operating conditions. In fact, manufacturing variations from system to system can result in fluence variation of 15% or more among different laser treatment systems. Furthermore, the individual technique used by the user delivering the treatment, can also affect the treatment, e.g., by different pressures applied to the skin surface which in turn affects, for instance, blood perfusion at the treatment site.

In laser treatment of acne, the operating thermal range is generally bound on the upper end at the epidermis and dermis damage threshold temperature, and at the lower end by the temperature required to bring the sebaceous gland to its damage threshold temperature. While there is currently not a good way to directly measure the temperature of the sebaceous gland being targeted by the treatment protocol, the skin surface temperature can be an indicator of the sebaceous gland temperature. A correlation model providing the correspondence between sebaceous gland temperature and skin surface temperature can then be used to tailor the actual treatment protocol using skin surface temperature measurements for effectively targeting sebaceous gland damage while staying below the damage threshold for the epidermis. The correlation model can be developed using, for example, an analytical heat transfer model, or by using clinical data (e.g., via biopsies) correlating skin surface temperature to sebaceous gland damage given the application of a specific treatment protocol.

Based on clinical data, the operating temperature range for acne treatment expressed in terminal skin surface temperature, using for example the treatment protocol illustrated in FIGS. 3 and 4, is approx. 45° C. to 55° C. At skin surface temperatures below 45° C., it has been determined that there is no damage to the sebaceous gland. When the skin surface temperature is between 45° C. and 55° C., there are varying degrees of sebaceous gland damage, with no epidermal damage. Above 55° C., there is epidermal damage in addition to damage to the sebaceous gland.

However, clinical data also indicates that terminal skin surface temperature has a strong dependence on tissue parameters at the specific treatment area for a particular individual. While existing treatment protocols have been based on a "one treatment fits all" type of an approach, an innovative analysis protocol can be incorporated into the treatment method so as to directly determine individually tailored treatment parameters extrapolating from measurements of terminal skin temperature at lower laser powers and/or the skin surface temperature reached during an initial part of a treatment and/or the terminal skin surface temperatures reached during previous treatments, to avoid epidermis damage while efficaciously causing sebaceous gland damage. In this way, the treatment protocol can be customized for a specific treatment area for a particular individual, and also mitigates treatment variations that can be caused by variations in the laser power output of a specific machine, as well as variations in treatment conditions, such as ambient humidity and temperature. Therefore, it would be desirable to optimize the treatment protocol for different subjects and even different tissue locations for the same subject so as to not cause unwanted tissue damage, while still effectively treating the target tissue component (e.g., the sebaceous gland).

For instance, by directly measuring the skin surface temperature during the first four pulses of FIG. 3, the maximal epidermal surface temperature after application of subsequent pulses can be predicted with a high degree of accuracy. This prediction can be used for real time modification of the specific treatment protocol for a particular area of the skin, such as reducing the number of pulses applied, adjusting the pulse widths, or modifying the laser power, for the subsequent pulses. If the laser system incorporates a cooling system that can react quickly enough, the cooling is also adjustable as part of the real time modification of the treatment system parameters. This customization process greatly enhances subject comfort and safety during the treatment procedure.

This analysis protocol can be performed by incorporating temperature measurements using, for example, a commercial, off-the-shelf, low-cost cameras that can be built into the scanner (e.g., see temperature sensor 206 of FIG. 2) that is held by the medical professional to apply the treatment to the subject, or by using a separate, commercial off-the-shelf single or multi-pixel thermal measurement device. The prediction process can be performed on a highly localized level, thus adjusting the treatment protocol on the fly or prior to the treatment commencement, even adjusting the protocol for each individual spot in a treatment matrix. In this way, the treatment protocol can be specified to provide the necessary treatment laser power while staying below the epidermis and dermis damage threshold temperature.

Figure 5:
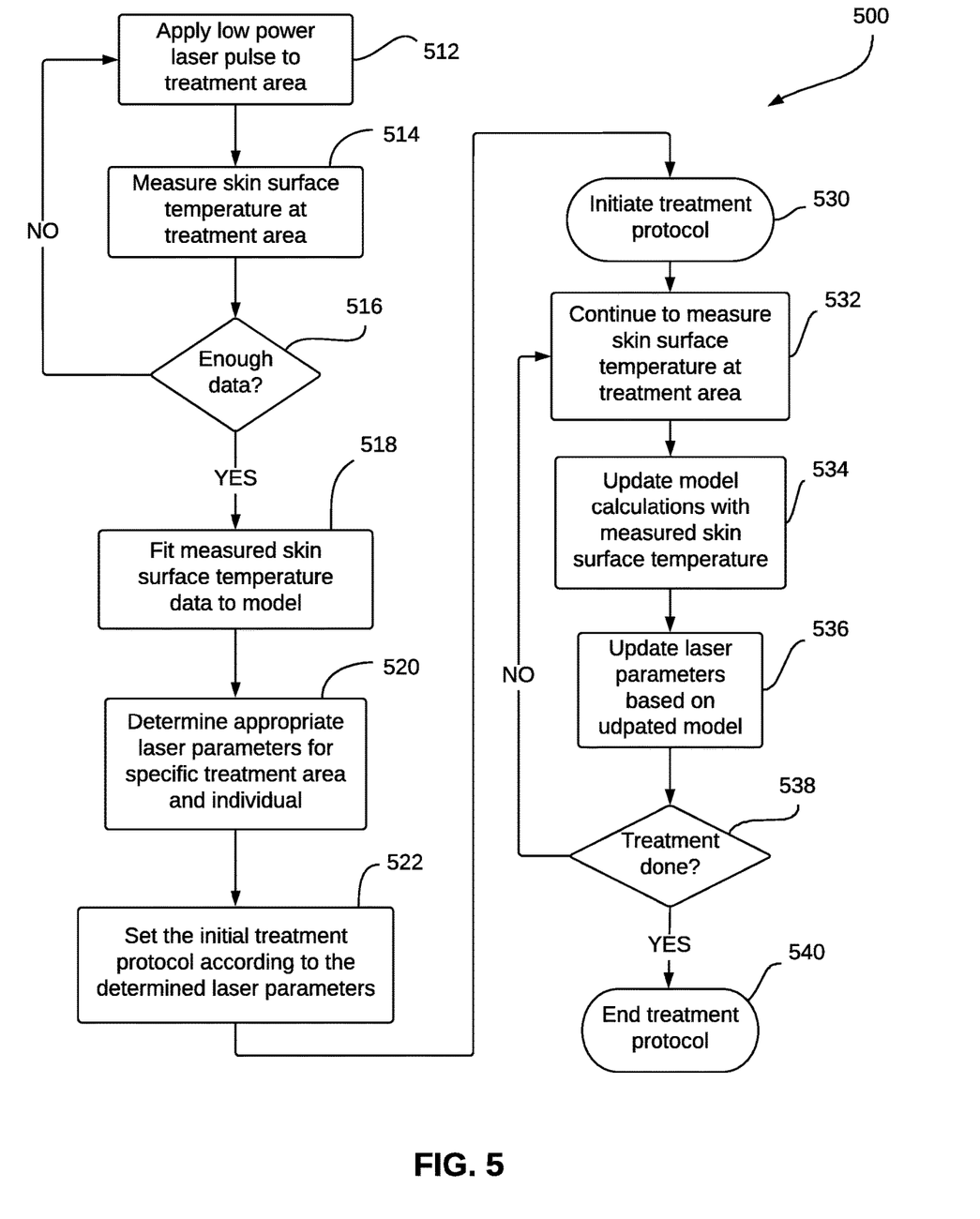
FIG. 5 shows a flow chart illustrating an exemplary process for analyzing the measured skin surface temperature, predicting the temperature of the skin when subsequent laser pulses and/or additional cooling are applied, then modifying the treatment protocol accordingly.

Turning to FIG. 5, a flow chart illustrating an exemplary process for the analysis protocol, in accordance with an embodiment. The analysis protocol assumes that the maximum epidermis temperature and the damage threshold temperature for the target (e.g., the sebaceous gland) are known. Additionally, a correlation model between the skin surface temperature and the target (e.g., the sebaceous gland) has been established using computational analysis, such as finite element modeling of the heat transfer for instance, or by clinical experiments using biopsies. Thus, knowledge of the target value for the terminal skin surface temperature is assumed for the analysis protocol. As an example, for the treatment protocol earlier described in FIGS. 3 and 4, it is known that the target peak skin surface temperature is 51° C.

As shown in FIG. 5, an analysis protocol 500 begins by applying a low power laser pulse to a treatment area in a step 512. The laser power should be set at values that are below the damage threshold for epidermis damage. The skin surface temperature at the treatment area is then measured in a step 514. The temperature measurement can be performed, for example, using a low speed infrared camera or similar apparatus. Then a determination is made in a decision 516 whether enough data has been collected to fit the collected data into the pre-established correlation model. If the answer to decision 516 is no, then the process returns to step 512, at which a laser pulse at a different, low power setting is applied to the treatment area to gather additional correlation data between applied laser power and epidermis temperature.

If the answer to decision 516 is yes, then analysis protocol 500 proceeds to fit the measured skin surface temperature data to the established correlation model in a step 518. Next, the appropriate laser parameters for the specific treatment area for the particular individual are determined in a step 520. Finally, in a step 522, the exact treatment protocol to be used for the specific treatment area for the particular individual is modified according to the appropriate laser parameters found in step 520.

Continuing to refer to FIG. 5, optionally, analysis protocol 500 can be continued during the actual treatment protocol. In an exemplary embodiment, following the setting of the laser parameters in step 522, a treatment protocol with the appropriate laser parameters is initiated in a step 530. Then, in a step 532, the process continues to measure the skin surface temperature at the treatment area. The measured skin surface temperatures are used to update the correlation model calculations in a step 534, and the laser parameters for the treatment protocol are updated based on the updated calculations in a step 536. Then a decision 538 is made to determine whether the treatment protocol (i.e., the number of laser pulses to be applied to the treatment area) is complete. If the answer to decision 538 is NO, then the analysis protocol returns to step 532 to continue measuring the skin surface temperature. If the answer to decision 538 is YES, then the treatment protocol is terminated in a step 540.

In other words, until the treatment protocol is complete, analysis protocol 500 can implement optional steps 530 through 540 to continue adjusting the laser parameters even during the actual treatment protocol. In fact, if other relevant data regarding the subject, such as laser settings from prior treatments in the same treatment area for the same subject, exist, they can also be fed into the model calculations for further refinement of the laser parameters.

Figure 6:
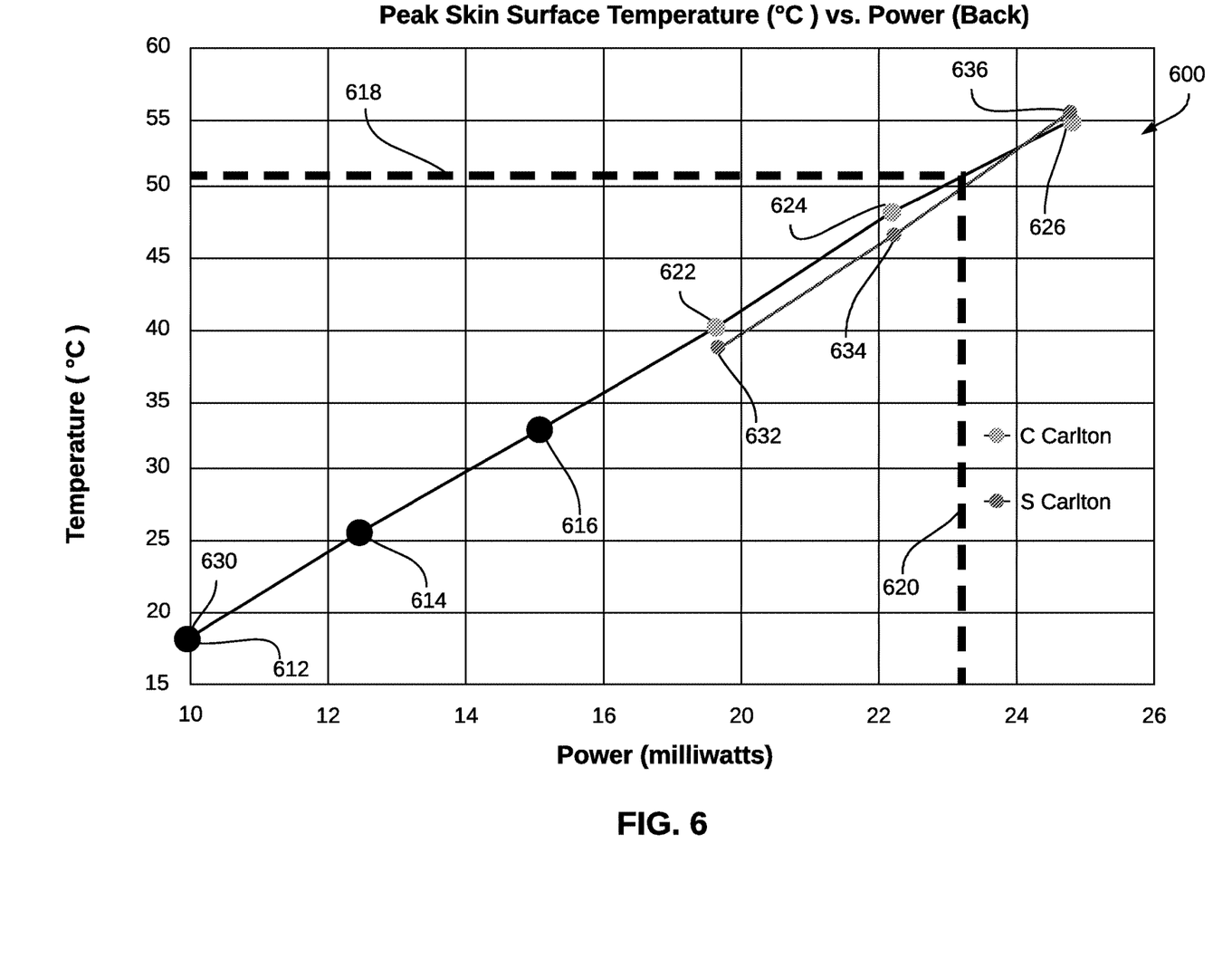
FIG. 6 shows the measured skin surface temperature for various applied laser pulse powers at similar treatment areas for two different individuals.

Turning now to FIG. 6, an example of the analysis protocol and subsequent treatment protocol are shown, in accordance with an embodiment. A graph 600 shows the relationship between laser power and peak skin surface temperature during application of a series of laser pulses on two different subjects, identified as "C Carlton" and "S Carlton." Large dots 612, 614, and 616 show the initial three low power laser pulses applied to subject "C Carlton," after which the analysis protocol described above is used to predict peak skin surface temperature as measured by an IR camera, thus defining a safe operating range as indicated by a dashed horizontal line 618 and a dashed vertical line 620. Dots 622, 624, and 626 show data take at slightly higher laser power settings on same subject "C Carlton."

Continuing to refer to FIG. 6, in order to determine the applicability of the same dosimetry determination process on a different subject, the same power laser pulses were applied to a second subject "S Carlton," starting with a similar starting temperature as shown by a dot 630. On the second subject "S Carlton," a treatment protocol of increasing laser power was immediately applied, without the dosimetry protocol at lower temperatures, as shown by dots 632, 634, and 636. While the actual measured epidermis temperature for second subject "S Carlton" differed from those of first subject "C Carlton," graph 600 indicates that the safe operating range, indicated by dashed lines 618 and 620, would have been also applicable for second subject "S Carlton" as well. In this way, the analysis protocol described above takes into consideration these individual differences in tailoring the treatment protocol for a specific treatment area on a particular individual. The efficacy of the analysis protocol has been verified with in vivo data.

The analysis protocol can be performed in advance of the actual treatment session, for example, as the subject is being checked in at an appointment or in a pre-treatment session. As low powers are used, the analysis protocol can be performed without the need for local anesthesia, with virtually no epidermal or dermal damage occurring during the application of the analysis protocol. For instance, in preparation for treatment, a trained operator can quickly pre-measure the various treatment locations and, with one scan per skin location, develop an individualized treatment protocol.

Once a relationship between laser power and the resulting skin surface temperature has been established for a particular subject, and/or a particular skin location, and/or a particular laser device, this relationship, indicated by the slope of the line connecting dots 612, 614, 616, 622, 624, and 626 in FIG. 6, can be used to continuously adjust future treatments. Furthermore, as the treatment schedule proceeds, all of the treatment data can be added to the basis for establishing the skin surface versus power correlation. In this way, the correlation is continually updated and refined, even after the treatment protocol is initiated. For instance, based on the known relationship between laser power and resulting skin surface temperature reached at a particular treatment location, a suggestion for adjusting the laser parameters, such as the laser power can be given to the dermatologist for manual adjustment, or the device can automatically adjust e.g. the laser power, for the next treatment location.

The concept of the analysis protocol described above can be extended to real-time adjustment of the treatment protocol using a closed-loop control process. The surface temperature of the skin can be measured using, for example, an infrared (IR) camera or other temperature measurement mechanisms. By fitting the measured temperature to a mathematical model of the skin tissue, for instance, the measured skin surface temperature can be correlated to the temperature of the target component, such as the sebaceous gland, which cannot be directly measured.

That is, in accordance with another embodiment, a system whereby temperature measurements of a skin surface during initial parts of a treatment for a specific location are used to predict future temperatures of the skin surface at this specific location. The future temperatures, so predicted, are used to adjust a thermal energy delivered by a laser, or lasers, by adjusting one or more parameters, such as laser power, pulse width, number of pulses, and others that affect the thermal energy delivered by the laser, or by adjusting one or more parameters of a cooling system, such as air flow, such that the future temperature of the skin surface for the specific location, and thereby the temperature of the underlying regions and components of the tissue, which cannot be readily measured in a direct manner, reaches a desired value or does not exceed a specified value.

In other words, the dosimetry (e.g., the settings of the light treatment including, for example, power settings for the laser light source) administered to the subject) can be adjusted in real-time by using a predictive control process. For instance, by directly measuring the skin temperature during pulses 322, 324, and 326 shown in FIG. 3, a predicted maximal epidermal surface temperature after application of subsequent pulses can be calculated with a high degree of accuracy. This prediction is accomplished by fitting a mathematical function to the measured epidermal surface temperatures following the application, for example, of three or four treatment pulses. The suitable mathematical function is in turn selected based on knowledge of the pulsing scheme used in the treatment protocol. For example, for the treatment protocol shown in FIG. 3, a single exponential function can provide an accurate model of the skin surface temperature following subsequent treatment pulse applications. This prediction can then be used in modifying the specific treatment protocol for a particular area of the skin in real time. For instance, the user can modify one or more of the number of additional pulses applied, as well as pulse width and laser power of subsequent pulses. Additionally, if the photo-treatment system includes a sufficiently responsive cooling unit, the cooling applied to the treatment area is also adjustable as a part of the real time modification of treatment system parameters. This customization process greatly enhances patient comfort and safety during the treatment procedure.

The analysis for use in the predictive control process can be performed using a temperature measurement device, for example, a commercial, off-the-shelf, low-cost camera incorporated into the scanner (e.g., temperature sensor 206 of FIG. 2) or by using a separate thermal measuring device, such as a single- or multi-pixel thermal imager. By controlling the size of the target treatment area and specifically measuring the skin surface temperature at the target treatment area, the prediction process can be performed on a highly localized level, thus enabling the medical professional administering the treatment protocol to make adjustments prior to the start of the treatment protocol, in real time during the treatment, or even for each individual spot in a treatment matrix. In this way, the treatment protocol can be administered in a highly customizable way to provide the necessary treatment laser power while staying below the epidermis and dermis damage threshold temperature.

For instance, the Arhenius damage function yields that target damage is exponentially related to peak temperature; subsequently, the peak temperature of the skin surface is correlated to the peak temperature of the target component. In an example, the temperature rise is approximately 180° C./second for irradiation with a 22 W laser over a 5 mm-by-5 mm spot with a 150 ms pulse; in this case, the skin surface measurement should be updated approximately every 2.5 ms, or at 400 Hz, in order for the temperature measurement is to be used as a control input for the treatment protocol. With such a fast temperature measurement method, the laser can be shut off when the measured skin surface temperature reaches a preset threshold value.

Alternatively, a slower temperature measurement device can be used to predict the peak temperature by measuring the temperature rise and fall behavior during the early pulse application in the treatment protocol. The skin surface temperature can be measured during the first few laser pulses applied at the treatment area, and the temperature measurements are used to extrapolate the expected skin surface temperature during subsequent pulse applications such that the energy profile of the subsequent pulses can be adjusted accordingly. For instance, laser parameters such as the laser pulse duration, power, and pulse interval can be adjusted in order to deliver the appropriate amount of energy to the target chromophore while avoiding damage to the surrounding medium.

Figure 7:
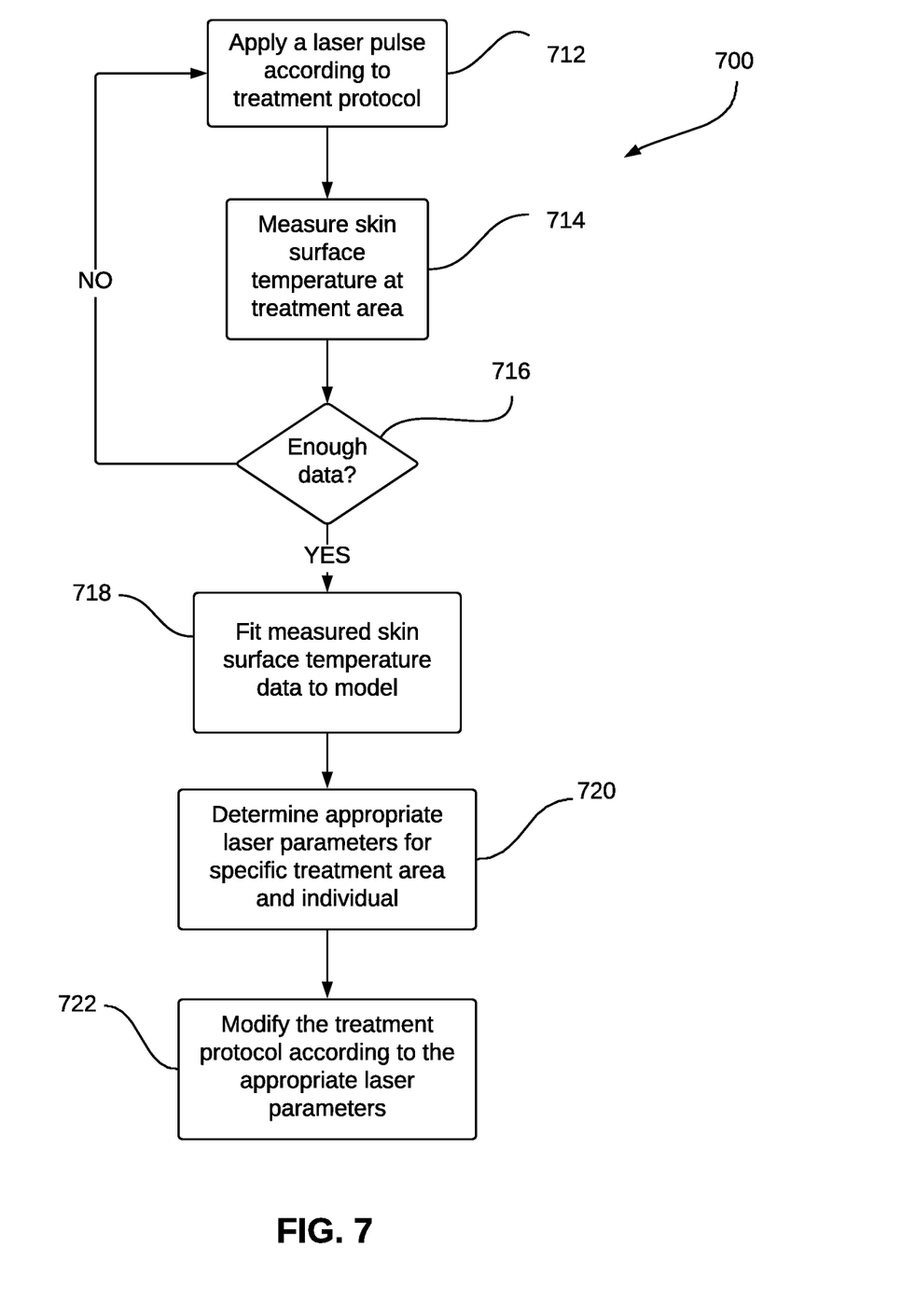
FIG. 7 shows a flow chart illustrating an exemplary process for a closed-loop control of the laser system parameters based on real-time skin surface temperature measurements, in accordance with an embodiment.

A flow chart shown in FIG. 7 illustrates an exemplary process for a closed-loop control of the laser system parameters based on real-time skin surface temperature measurements, in accordance with an embodiment. A process 700 begins with the initialization of the laser treatment protocol with the laser system set at treatment settings (i.e., therapeutic levels of power, pulse width, etc.). In a step 712, a laser pulse is applied to a treatment area in accordance with a treatment protocol. The treatment protocol can involve, for example, the application of pulses of sequentially increasing power, or pulses of substantially identical power settings repeatedly applied to the treatment area. An example treatment protocol involves the repeated application of laser pulses from a 22 W laser with a 5-millimeter by 5-millimeter spot size and 150 ms duration.

Continuing to refer to FIG. 7, during the application of each laser pulse, the skin surface temperature at the treatment area is measured in a step 714. Optionally, the skin surface temperature is measuring during the cooling down periods between the pulses. The measurement can be made, for example, by a 25 Hz refresh rate infrared camera. Faster devices, such as a 400 Hz refresh rate temperature measurement device, can be used for more accurate measurement of the skin surface temperature at and following the application of the laser pulses.

Then a determination is made in a decision 716 whether enough skin surface temperature data has been gathered for curve-fitting purposes. If the answer to decision 716 is NO, then the process returns to step 712 for the application of another laser pulse. If the answer to decision 716 is YES, then the measured skin surface temperature data are fitted to a predictive model in a step 718. Curve-fits of the maximum and, optionally, minimum skin surface temperatures are generated during step 718. The predictive model can be generated, for instance, by compiling a large number of temperature measurements corresponding to the application of laser pulses to test subjects in clinical settings, or by analytical modeling of the tissue.

Based on the curve-fits generated in step 718, a determination is made in a step 720 for the appropriate laser parameters for the specific treatment area on the individual being treated. For example, if the curve-fits predict the skin surface temperature will rise above a predetermined threshold temperature, such as 45° C., then the laser parameters are adjusted to reduce the laser power. In this case, the skin surface temperature measurements can indicate that the specific treatment area on the subject is particularly sensitive to laser pulse energy absorption. Alternatively, if the curve-fits predict the desired temperature, such as 55° C. for target chromophore damage, will not be reached with the current laser pulse power settings, then the laser parameters can be adjusted to provide the necessary treatment power. Such a situation can occur if the epidermis and dermis characteristics are such that the specific treatment area does not readily absorb the laser pulse energy.

Figure 8:
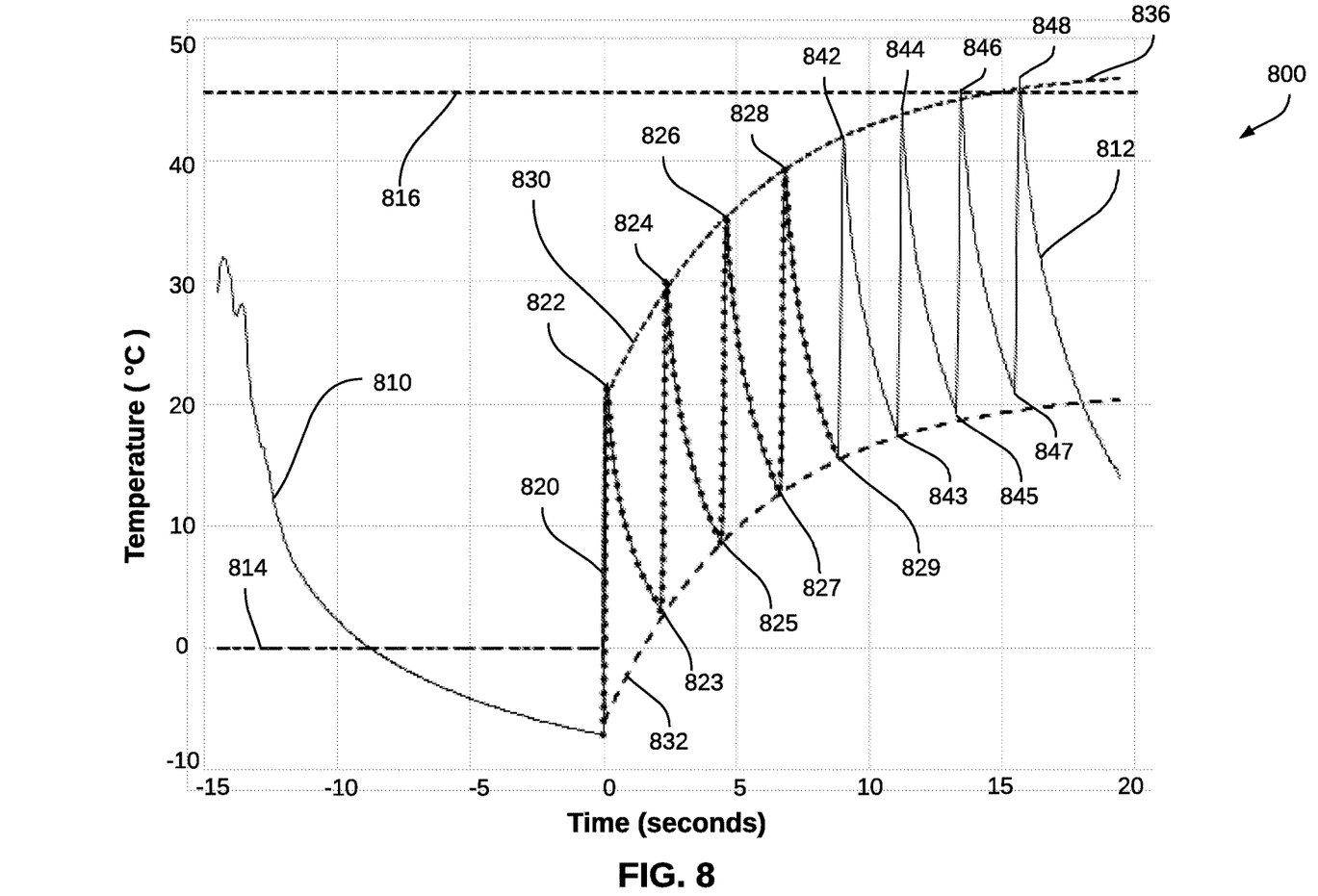
FIG. 8 shows the measured skin surface temperature resulting from the application of four pulses to a treatment area that are used as data for predicting the subject's skin temperature rise with subsequent pulse application, as well as the resulting curve fit and actual temperature measurements, in accordance with an embodiment.

FIG. 8 illustrates an exemplary predictive closed-loop control process based on measured skin surface temperature resulting, in accordance with an embodiment. A graph 800 in FIG. 8 shows the various temperature measurements and calculated curves as a function of time that are used in the predictive closed-loop control process, such as illustrated in FIG. 7. In FIG. 8, time zero corresponds to the moment of application of the first laser pulse (from a 22 W laser, 150 ms pulse and a 5-millimeter by 5-millimeter square spot, in this case) preceded by approximately 15 seconds of air cooling (i.e., time −15 to zero). The air cooling is applied to the treatment area throughout the laser pulse application in the present example. The skin surface temperature is measured using a 25 Hz update rate IR camera in the present example, although the use of other temperature measurement devices is contemplated.

Continuing to refer to FIG. 8, the measured skin surface temperature during the initial cooling is shown by a curve 810. The measured skin surface temperature during the application of laser pulses is shown by curve 812. The target skin surface temperature is indicated by a dashed line 816, shown here at 45.5° C.

Starting at time zero, the first temperature measurements after the first four pulses (indicated by circular dots) are fitted to a predictive model. Specifically, in the example shown in FIG. 8, the peak temperatures as well as the cooled down temperature immediately preceding the next pulse application are fitted into a clinically-generated predictive model. Maximum temperature peaks 822, 824, 826, and 828, as well as minimum temperature nadirs 823, 825, 827, and 829, are curve fitted to generate a maximum temperature curve 830 and a minimum temperature curve 832 (shown as dashed curves). Optionally, the temperature measurements made during the cooling down periods between the laser pulse applications are used to improve the measurement accuracy of the maximum temperature peaks as well as the minimum temperature nadirs.

The skin surface temperatures are measured during subsequent laser pulse applications, as shown in curve 812. It can be seen that the maximum and minimum temperature curves 830 and 832 accurately track the measured skin surface temperatures (i.e., peaks 842, 844, 846, and 848 and nadirs 843, 845, and 847 of curve 812). It is noted that the predicted temperature rise (i.e., dashed curve 830) and the actual measured temperatures (specifically peaks 846 and 848) indicate the desired temperature of 45.5° C. has been achieved by the application of pulses 6 and 7, thus the laser treatment protocol is halted without the application of an eighth pulse.

Even with a relatively slow temperature measurement device, such as a 25 Hz refresh IR camera, fitting the temperature data during the cooling down periods between laser pulse applications allows for a good estimation of the rapid temperature rise achieved with each pulse application. If a faster temperature measurement device (e.g., 400 Hz refresh rate or faster) is used, then the temperature profiles can be directly measured in real time.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. For example, lasers with other wavelengths, such as around 1210 nm, can be used. Alternatively, the pre-treatment analysis method described above can be used with other treatment protocols, such as those described in WIPO Patent Application WO/2018/076011 to Sakamoto et al. and WIPO Patent Application WO/2003/017824 to McDaniel. In fact, the method is applicable to any thermal treatment protocol involving equipment that may be subject to system, user, atmospheric conditions, and other variability from treatment to treatment.

Accordingly, many different embodiments stem from the above description and the drawings. It will be understood that it would be unduly repetitious and obfuscating to literally describe and illustrate every combination and subcombination of these embodiments. As such, the present specification, including the drawings, shall be construed to constitute a complete written description of all combinations and subcombinations of the embodiments described herein, and of the manner and process of making and using them, and shall support claims to any such combination or subcombination.

For example, embodiments such as the below are contemplated:

1. A method for determining a suitable set of parameters for a light source within a photo-thermal targeted treatment system for targeting a chromophore embedded in a medium, the method including, prior to administering a treatment protocol: 1) administering at least one laser pulse at a preset power level to a location to be treated, the preset power level being below a known damage threshold; 2) measuring a skin surface temperature at the location to be treated, following administration of the at least one laser pulse; 3) estimating a relationship between the parameters of the light source and the skin surface temperature; and 4) defining a safe operating range for the parameters of the light source in order to avoid thermal damage at the location to be treated.

2. The method of Item 1, wherein steps 1) through 4) are performed on a first subject for a first treatment area, then steps 1) through 4) are repeated on the first subject for a second treatment area.

3. The method of Item 1, wherein steps 1) through 4) are performed on a first subject for a treatment area, then steps 1) through 4) are repeated on a second subject for the treatment area.

4. The method of Item 1, further including taking into consideration treatment data from previous treatments for the same subject.

5. The method of Item 1, wherein steps 2) through 4) are repeated while the actual treatment protocol is performed on the subject.

6. A system whereby temperature measurements of a skin surface during initial parts of a treatment for a specific location are used to predict future temperatures of the skin surface at this specific location. The future temperatures, so predicted, are used to adjust a thermal energy delivered by a laser, or lasers, by adjusting one or more parameters, such as laser power, pulse width, and others that affect the thermal energy delivered by the laser or lasers, or by adjusting one or more parameters of a cooling system, such as air flow, such that the future temperature of the skin surface for the specific location, and thereby the temperature of the underlying regions and components of the tissue, which cannot be readily measured in a direct manner, reaches a desired value.

7. A system whereby temperature measurements of a skin surface taken during a treatment of an adjacent area, or areas, are used to predict future temperatures of the skin surface at this specific location. The future temperatures, so predicted are used to adjust a thermal energy delivered by a laser, or lasers, by adjusting one or more parameters such as laser power, pulse width, and others that affects the thermal energy delivered by the laser or lasers, or by adjusting one or more parameters of the cooling system, such as air flow, such that the future skin surface temperature for the specific location, and thereby the temperature of the underlying regions and components of the tissue, which cannot be readily measured in a direct manner, reaches a desired value.

In the specification, there have been disclosed embodiments of the invention and, although specific terms are employed, they are used in a generic and descriptive sense only and not for purposes of limitation. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for determining a suitable set of parameters for operating a light source within a photo-thermal targeted treatment system for targeting a chromophore embedded in a medium, the method comprising:
   a. cooling a first treatment location;
   b. administering a first set of laser pulses from the light source at the first treatment location, the first set of laser pulses having thermal energy below a known damage threshold of the medium;
   c. tracking skin surface temperatures at the first treatment location at a refresh rate of 25 Hz to 400 Hz while administering the first set of laser pulses;
   d. estimating a relationship between parameters for operating the light source and the skin surface temperature at the first treatment location by fitting the skin surface temperature to a correlation model;
   e. using the correlation model, determining a safe operating range for the parameters for operating the light source to avoid thermal damage to the medium at the first treatment location while still effectively targeting the chromophore;
   f. administering a second set of laser pulses from the light source at the first treatment location, the second set of laser pulses having thermal energy at least at a known damage threshold of the chromophore while staying within the safe operating range for the parameters for operating the light source; and
   g. adjusting the parameters for operating the light source according to the tracked skin surface temperatures at the first treatment location to stay within the safe operating range.

2. The method of claim 1, further comprising repeating steps a.-g. at a second treatment location on the first subject.

3. The method of claim 1, further comprising repeating steps a.-g. on a second subject.

4. The method of claim 1, wherein adjusting the parameters for operating the light source includes adjusting at least one of laser power, pulse width, pulse interval, maximum power output, and a skin surface cooling mechanism used for performing the cooling.

5. A method for treating a subject with a photo-thermal targeted treatment system including a light source for targeting a chromophore embedded in a medium, the method comprising:
   a. cooling a first treatment location of the subject from a first surface temperature to a second surface temperature;
   b. administering a laser pulse from the light source to the first treatment location;
   c. during application of the laser pulse, tracking skin surface temperatures at the first treatment location using an infrared camera operating at a refresh rate of 25 Hz to 400 Hz; and
   d. terminating a treatment protocol based at least in part on the skin surface temperatures so measured.

6. The method of claim 5, wherein cooling the first treatment location includes cooling the first treatment location from the first surface temperature of body temperature to second surface temperature less than body temperature.

7. The method of claim 5, wherein cooling includes using a contact cooling mechanism.

8. The method of claim 5, wherein terminating the treatment protocol includes fitting the skin surface temperatures so tracked to a model, determining appropriate laser parameters for the light source, and modifying the treatment protocol according to the appropriate laser parameters.

9. The method of claim 8, wherein terminating the treatment protocol further includes determining appropriate cooling parameters for a cooling mechanism, and modifying the cooling parameters during the treatment protocol.

10. The method of claim 5, wherein terminating the treatment protocol includes fitting the skin surface temperatures so tracked to a model, predicting a peak skin surface temperature, and adjusting at least one of laser power, pulse width, number of pulses, and cooling system parameters.

11. The method of claim 10, wherein the peak skin surface temperature is a temperature in a range of 45° C. and 55° C.

12. The method of claim 5, wherein a pulse duration of the laser pulse is 150 milliseconds.

13. The method of claim 5, further comprising repeating steps b.-d., wherein each repetition of steps b.-d. is performed for an individual spot in a treatment matrix.

14. The method of claim 5, wherein the treatment protocol includes determining a thermal energy to be provided by the laser pulse to damage a target chromophore while avoiding damage to a medium surrounding the target chromophore.

15. The method of claim 5, wherein the light source operates at a wavelength of 1720 nm.

16. The method of claim 5, wherein the light source operates at a wavelength of 1210 nm.

17. The method of claim 5, wherein the chromophore is a sebaceous gland embedded within a dermis with an overlying epidermis, and terminating the treatment protocol includes terminating the laser pulse based on the skin surface temperatures so tracked reaching a terminal skin surface temperature indicative of damage to the sebaceous gland without damage to the epidermis.

18. The method of claim 5, further comprising continuing to cool the first treatment location after terminating the treatment protocol.

* * * * *